US009108355B2

(12) United States Patent
Kume et al.

(10) Patent No.: US 9,108,355 B2
(45) Date of Patent: Aug. 18, 2015

(54) METHOD FOR PRODUCING SURFACE SHEET USING EMBOSS ROLLER

(75) Inventors: Yukio Kume, Tokyo (JP); Takako Fujii, Tokyo (JP); Yunfu Li, Tokyo (JP)

(73) Assignee: DAIO PAPER CORPORATION, Ehime (JP)

( * ) Notice: Subject to any disclaimer, the term of this patent is extended or adjusted under 35 U.S.C. 154(b) by 730 days.

(21) Appl. No.: 13/264,929

(22) PCT Filed: Apr. 15, 2009

(86) PCT No.: PCT/JP2009/057616
§ 371 (c)(1),
(2), (4) Date: Nov. 21, 2011

(87) PCT Pub. No.: WO2010/119535
PCT Pub. Date: Oct. 21, 2010

(65) Prior Publication Data
US 2012/0059343 A1    Mar. 8, 2012

(51) Int. Cl.
*B29C 59/04* (2006.01)
*A61F 13/475* (2006.01)
*A61F 13/511* (2006.01)
(Continued)

(52) U.S. Cl.
CPC ............. *B29C 59/04* (2013.01); *A61F 13/4756* (2013.01); *A61F 13/51104* (2013.01); *B29C 53/24* (2013.01); *B29C 65/02* (2013.01); *B29C 65/18* (2013.01); *B29C 66/21* (2013.01); *B29C 66/221* (2013.01); *B29C 66/438* (2013.01); *B29C 66/83411* (2013.01); *B29C 66/83415* (2013.01); *B29C 66/83511* (2013.01); *B32B 38/06* (2013.01); *B29K 2023/06* (2013.01); *B29K 2023/083* (2013.01); *B29K 2023/12* (2013.01); *B29K 2067/00* (2013.01); *B29K 2077/00* (2013.01); *B29K 2105/0854* (2013.01); *B29K 2311/10* (2013.01); *B29L 2016/00* (2013.01);
(Continued)

(58) Field of Classification Search
None
See application file for complete search history.

(56) References Cited

U.S. PATENT DOCUMENTS 7,338,700 B2    3/2008  McKenna et al.
2004/0116029 A1*  6/2004  Kelly et al. ................... 442/394
(Continued)

FOREIGN PATENT DOCUMENTS

EP    0 338 792    10/1989
GB    2 166 690     5/1986
(Continued)

*Primary Examiner* — Barbara J Musser
(74) *Attorney, Agent, or Firm* — Jordan and Hamburg LLP

(57) ABSTRACT

An emboss roller is provided that can give projecting-and-recess embosses to a surface sheet while uniform fiber density is realized through in an emboss roller which has a first emboss roll and a second roll formed as a set and gives projecting-and-recessed embosses by passing a surface sheet between these emboss rolls, and on the surface of the first emboss roll, a projecting portion projecting outward from a reference surface with the reference surface as a boundary and a recess portion recessed from the reference surface are provided, and the smooth reference surface is present in the periphery of the projecting portion and the recess portion, and on the surface of the second emboss roll, a projecting portion projecting outward from the reference surface with the reference surface as a boundary and meshed with the recess portion of the first emboss roll and a recess position recessed from the reference surface and meshed with the projecting portion of the first emboss roll are provided, and the smooth reference surface is present in the periphery of the projecting portion and the recess portion.

1 Claim, 10 Drawing Sheets

(51) Int. Cl.
*B29C 53/24* (2006.01)
*B29C 65/02* (2006.01)
*B29C 65/18* (2006.01)
*B29C 65/00* (2006.01)
*B32B 38/06* (2006.01)
B29K 23/00 (2006.01)
B29K 67/00 (2006.01)
B29K 77/00 (2006.01)
B29K 105/08 (2006.01)
B29K 311/10 (2006.01)
B29L 16/00 (2006.01)
B29L 31/48 (2006.01)

(52) U.S. Cl.
CPC .... *B29L 2031/4878* (2013.01); *Y10T 156/1023* (2015.01); *Y10T 156/125* (2015.01)

(56) References Cited

U.S. PATENT DOCUMENTS

| | | | |
|---|---|---|---|
| 2004/0161586 A1* | 8/2004 | Cree et al. | 428/131 |
| 2005/0136225 A1* | 6/2005 | McKenna et al. | 428/174 |
| 2008/0108962 A1 | 5/2008 | Furuta et al. | |
| 2010/0249740 A1* | 9/2010 | Miyamoto et al. | 604/384 |

FOREIGN PATENT DOCUMENTS

| | | |
|---|---|---|
| JP | 2000-071356 | 3/2000 |
| JP | 2004-174234 | 6/2004 |
| JP | 2006-115974 | 5/2006 |
| JP | 2009-050538 | 3/2009 |
| WO | WO-2006/043453 | 4/2006 |

* cited by examiner

Fig. 7(A)    FIRST EMBOSS ROLL    SECOND EMBOSS ROLL
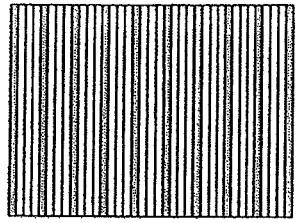 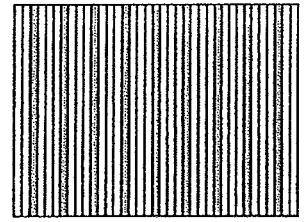
Fig. 7(B)    FIRST EMBOSS ROLL    SECOND EMBOSS ROLL
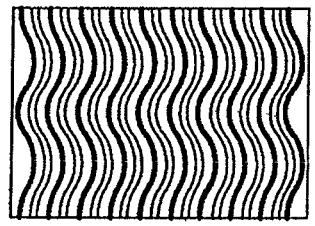 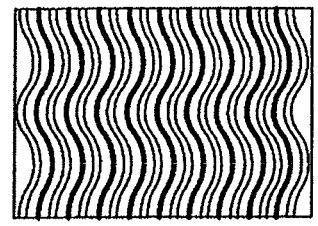
Fig. 7(C)    FIRST EMBOSS ROLL    SECOND EMBOSS ROLL
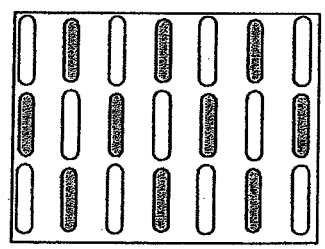 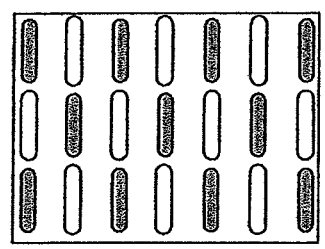

Fig. 8(A)
FIRST EMBOSS ROLL
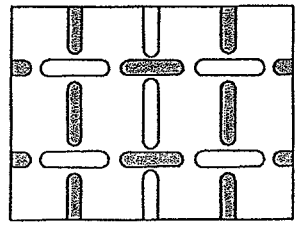
SECOND EMBOSS ROLL
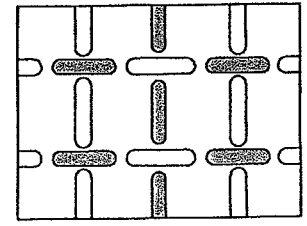
Fig. 8(B)
FIRST EMBOSS ROLL
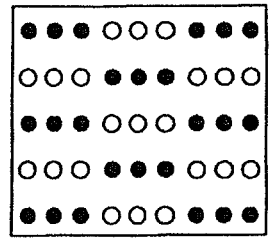
SECOND EMBOSS ROLL
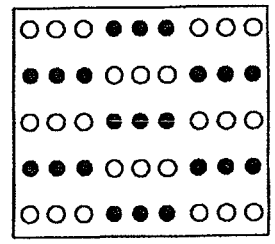

RELATED ART

RELATED ART

RELATED ART

METHOD FOR PRODUCING SURFACE SHEET USING EMBOSS ROLLER

BACKGROUND OF THE INVENTION

The present invention relates to an emboss roller that can give projecting-and-recessed embosses on a surface sheet and a method for producing a surface sheet which is rich in three-dimensional effects, has high cushion properties, eliminates skin trouble by reducing a contact area with the skin and is excellent in shape maintainability of the projecting-and-recessed embosses and the like.

Hitherto, surface materials of absorbent articles in which appropriate emboss patterns are given in accordance with various purposes such as suppression of a wet feeling by reducing a contact area with skin or improvement of texture and touch on the skin have been offered in the market. This type of articles includes those described in Japanese Unexamined Patent Application Publication No. 2004-174234 and Japanese Unexamined Patent Application Publication No. 2009-50538, for example.

Japanese Unexamined Patent Application Publication No. 2004-174234 proposes a surface sheet 50 for an absorbent article used on a skin contact surface of the absorbent article as illustrated in FIG. 9, which has an upper layer 51 made of a sheet-shaped article directed to the skin side of a wearer and substantially not expanding or contracting and a lower layer 52 made of a sheet-shaped article disposed on the absorber side and substantially not expanding or contracting, in which the upper layer 51 and the lower layer 52 are partially joined and a large number of joined portions are formed, the upper layer 51 projects toward the skin side of the wearer in a portion other than the joined portions and has a large number of projecting portions formed with hollow insides, the projecting portions and the joined portions are arranged alternately and forming a row in one direction, a plurality of the rows is provided, and with respect to any projecting portion in one row, a projecting portion is not located at a position adjacent to the one projecting portion in the right and left rows adjacent to the row. In a method for producing this surface sheet, as illustrated in FIG. 10, the upper layer 51 is shaped with projections and recesses by meshing the upper layer 51 with a meshed part between a first roll 53 having a peripheral face with a projecting-and-recessed shape and a second roll 54 having a projecting-and-recessed shape meshed with the projecting-and-recessed shape of the first roll 53 on the peripheral face, the lower layer 52 is overlapped while the upper layer 51 in the projected-and-recessed shaped state is held on the peripheral face in the first roll 53 through suctioning, and the lower layer 52 is joined to the upper layer 51 located above the projecting portion in the first roll 53. An enlarged view of an essential part of the first roll 53 is illustrated in FIG. 11.

Also, in Japanese Unexamined Patent Application Publication No. 2009-50538, as illustrated in FIG. 12, a sheet 60 for an absorbent article is proposed in which a first sheet 61 having an outer layer and an inner layer is intermittently joined to a second sheet 62 on the inner layer side, projecting portions projecting to the first sheet 61 side formed between the joined portions are consecutively provided on the sheet 60 for an absorbent article, and fibers constituting the outer layer of the first sheet 61 are fibers thinner than the fibers constituting the inner layer. In a producing method thereof, as illustrated in FIG. 13, first, the first sheet 61 is fed out of an original fabric, and the second sheet 62 is fed out of the original fabric at the same time. The fed-out first sheet 61 is meshed with a meshed portion $P_1$ between a first roll 63 having a projecting-and-recessed shape on the peripheral face and a second roll 64 having the projecting-and-recessed shape, which is a shape meshed with the projecting-and-recessed shape, on the peripheral face so as to shape the first sheet 61 with projections and recesses. The first sheet 61 which was shaped with projections and recesses by meshing between the first roll 63 and the second roll 64 is brought into close contact with the peripheral face of the first roll 63 by a suction force by a suction portion formed in the first roll 63, and the shaped state with projections and recesses are maintained. In the state in which the first sheet 61 is sucked and brought into close contact with the peripheral face of the first roll 63 at a merging portion $P_2$, the first sheet 61 is laminated with the second sheet 62 supplied separately, and the first sheet 61 and the second sheet 62 located at the distal end of a projecting portion of a gear of the first roll 63 are joined together by thermal fusion bonding. A compound sheet in which the first sheet 61 and the second sheet 62 are bonded together is heated and compressed again at a portion $P_3$ by the first roll 63 and a fourth roll 65 so that an adhesion force is improved appropriately and a firmly fixed joined portion is formed, and shape stability of the projection portion is maintained.

CITATION LIST

In the case of Japanese Unexamined Patent Application Publication No. 2004-174234 and Japanese Unexamined Patent Application Publication No. 2009-50538, by heat-sealing the lower-layer side sheets 52 and 62 on the bottom face of the recessed portion having the projecting-and-recessed shape on the upper-layer sheets 51 and 61, the projecting-and-recessed shape is maintained, which is an advantage.

However, since the projecting-and-recessed shape of the first rolls 53 and 63 and the second rolls 54 and 64 for shaping the projections and recesses on the upper-layer side sheets 51 and 61 forms a gear shape, there is a problem in which a fiber density of a portion constituting a wall surface of the projection portion becomes extremely smaller than the other portions or becomes uneven. That is, if an unwoven cloth enters the meshed portion between the first rolls 53 and 63 and the second rolls 54 and 64, the unwoven cloth is strongly pulled in an MD direction (channel direction) and a CD direction (direction orthogonal to the channel) due to the mesh between the gears and the fiber density becomes small and at the same time, since an application degree of a tensile stress is different between the walls opposing the MD direction and the CD direction, a difference occurs in the fiber density and the fiber density as a whole becomes uneven as a result.

SUMMARY OF THE INVENTION

Thus, a first object of the present invention is to provide an emboss roller which can give projecting-and-recessed embosses to the surface sheet while the uniform fiber density is realized.

Also, a second object is to provide a method for producing a surface sheet, using the emboss roller, which is rich in three-dimensional effects, has high cushion properties, minimizes a contact area with skin, effectively prevents skin trouble such as rubbing, rash, itches and the like, improves touch on the skin and eliminates a sticky feeling when a body fluid is absorbed and moreover, can sustainably maintain the projecting-and-recessed shape not only in a dry state but also while the body fluid is absorbed by improving shape retention of the projecting-and-recessed embosses and to obtain an absorbent article using the surface sheet.

In order to solve the above problems, as the present invention includes an emboss roller apparatus which has a first emboss roll and a second roll formed as a set and which imports projecting-and-recessed embosses to a surface sheet bypassing the surface sheet between these emboss rolls, the emboss roller set including, on the surface of the first emboss roll, a projecting portion projecting outward from a reference surface with the reference surface as a boundary and a recess portion recessed from the reference surface and a smooth reference surface present in the periphery of the projecting portion and the recess portion; and on the surface of the second emboss roll, a projecting portion projecting outward from the reference surface with the reference surface as a boundary and meshed with the recess portion of the first emboss roll and a recess portion recessed from the first reference surface and meshed with the projecting portion of the first emboss roll and a smooth second reference surface in the periphery of the projecting portion and the recess portion.

In a first aspect of the present invention, the emboss roller apparatus, on the surface of the first emboss roll, the projecting portion projecting outward from the reference surface with the reference surface as a boundary and the recess portion recessed from the reference surface are provided, and the smooth reference surface is provided in the periphery of the projecting portion and the recess portion and on the surface of the second emboss roll, the projecting portion projecting outward from the reference surface with the reference surface as a boundary and meshed with the recess portion of the first emboss roll and the recess portion recessed from the reference surface and meshed with the projecting portion of the first emboss roll are provided, and the smooth reference surface is provided in the periphery of the projecting portion and the recess portion.

Therefore, when a surface sheet of an unwoven cloth or the like enters between the first emboss roll and the second emboss roll and embosses are given to the surface sheet by a meshed portion between the projecting portion and the recess portion, since the smooth reference surface formed in the periphery of the projection portion and in the periphery of the recess portion is present, a tensile stress acting on the surface sheet is buffered by a stepped portion on the reference surface, and the fiber density can be prevented from becoming uneven. That is, if prior-art gear-shaped projections and recesses are meshed with each other, a mesh margin of a gear corresponding to the height dimension of the gear becomes a so-called driving force, generates a tensile stress in the surface sheet and shapes it in the projecting-and-recessed shape. However, if the tensile stress corresponding to the mesh margin acts at once, a portion where the fibers of the surface sheet are excessively pulled is generated, which results in a partially lowered fiber density. On the other hand, in the case of the present invention, since the smooth reference surface is present in the middle of the meshed portion between the recess portion and the projecting portion, the tensile stress is relaxed here, and the tensile stress is made to act in division into so-called two stages, and thus, the portion where the fibers are excessively pulled is eliminated and the partial drop in the fiber density is suppressed, and the projecting-and-recessed embosses can be given to the surface sheet while the fiber density is made uniform.

According to a second aspect of the invention, the emboss roller is provided in which the first emboss roll and the second emboss roll are juxtaposed vertically in upper and lower stages.

In the second aspect of the present invention, a device is provided in which the first emboss roll and the second emboss roll are juxtaposed vertically in upper and lower stages. If the surface sheet is to be conveyed in the same direction, the surface sheet is given the projecting-and-recessed embosses when passing between the first emboss roll and the second emboss roll at a stage when having circled only a half cycle around the first emboss roll and then, after having circled only a half cycle of the second emboss roll, the surface sheet is fed out in the conveying direction.

According to a third aspect of the present invention, a method for producing a surface sheet made of an upper layer sheet to which the projecting-and-recessed embosses are given and a planar shaped lower layer sheet and in which the bottom face of the recess portion of the upper layer sheet is heat-sealed with the lower layer sheet is provided, wherein in the emboss roller described above, an anvil roll having a smooth surface is arranged adjacent to the second emboss roll, and at least one of the second emboss roll and the anvil roll is brought into a state heated to a predetermined temperature;

the upper layer sheet is passed between the first emboss roll and the second emboss roll to be given the projecting-and-recessed embosses, and during a process of circling along the second emboss roll, the upper layer sheet is conveyed while the shape following the projecting-and-recessed portion of the second emboss roll is maintained and then, introduced between the second emboss roll and the anvil roll and overlapped with the lower layer sheet having entered between the second emboss roll and the anvil roll during a process of passing between the second emboss roll and the anvil roll, and the bottom face of the recess portion of the upper layer sheet and the lower layer sheet are heat-sealed.

The present invention according to the third aspect thereof produces the surface sheet made of the upper layer sheet given with the projecting-and-recessed embosses and the planar shaped lower layer sheet and in which the bottom face of the recess portion of the upper layer sheet and the lower layer sheet are heat-sealed by using the emboss roller described with respect to the first and second aspects of the present invention. First, in the emboss roller, the anvil roll having a smooth surface is arranged adjacent to the second emboss roll, and at last one of the second emboss roll and the anvil roll is brought into a heated state to a predetermined temperature. Then, the upper layer sheet is passed between the first emboss roll and the second emboss roll to be given the projecting-and-recessed embosses, and during the process of circling along the second emboss roll, the upper layer sheet is conveyed while the shape following the projecting-and-recessed portion of the second emboss roll is maintained and then, introduced between the second emboss roll and the anvil roll, overlapped with the lower layer sheet having entered between the second emboss roll and the anvil roll during the process of passing through the second emboss roll and the anvil roll, and the bottom face of the recess portion of the upper layer sheet and the lower layer sheet are heat-sealed.

If this method is used, the upper layer sheet can be joined to the lower layer sheet without crushing the embosses having a projecting shape formed on the upper layer sheet, and since the bottom face of the recess portion of the upper layer sheet and the lower layer sheet are heat-sealed, rich three-dimensional effects and high cushion properties are given, the contact area with skin is minimized, skin troubles such as rubbing, rash, itches and the like can be effectively prevented, touch on the skin is improved, a sticky feeling when the body fluid is absorbed is eliminated, and moreover, the projecting-and-recessed emboss shape can be sustainably maintained not only in the dry state but also while the body fluid is absorbed even after time has elapsed since manufacture. Also, since a hot-melt adhesive is not used, cost reduction can be realized, and skin troubles can be solved. Since the projecting shape is maintained in the favorable state without being crushed during the worn state, comfort can be also maintained for a long time.

According to a fourth aspect of the present invention, a method for producing the surface sheet is provided, in which the upper layer sheet and the lower layer sheet are both unwoven cloth.

The upper layer sheet and the lower layer sheet are both unwoven cloth. As a result, the touch on the skin becomes softer.

According to a fifth aspect of the present invention, a method for producing the surface sheet is provided, in which the upper layer sheet is an unwoven cloth, and the lower layer sheet is a mesh sheet.

As a result, while softness is maintained, reduction of remaining fluid and concealing properties of the body fluid are improved.

According to a sixth aspect of the present invention, a method for producing the surface sheet is provided, in which the upper layer sheet is a mesh sheet, and the lower layer sheet is an unwoven cloth.

As a result, a cool feeling generated by the mesh sheet is obtained, and a sticky feeling is solved.

According to a seventh aspect the present invention, an absorbent article is provided formed of the surface sheet obtained by the producing method described, a non-permeable back-face sheet, and an absorber interposed between the surface sheet and the non-permeable back-face sheet.

As described above in detail, according to the present invention, an emboss roller which can give projecting-and-recessed embosses to the surface sheet while uniform fiber density is realized can be provided.

Also, a surface sheet can be produced which is rich in three-dimensional effects, has high cushion properties, minimizes the contact area with skin, effectively prevents skin troubles such as rubbing, rash, itches and the like, improves touch on the skin, and eliminates a sticky feeling while the body fluid is absorbed, and by improving shape retention of the projecting-and-recessed embosses, the projecting-and-recessed shape can be sustainably maintained not only in the dry state but also while the body fluid is absorbed, and an absorbent article using the surface sheet can be obtained.

BRIEF DESCRIPTION OF DRAWINGS

FIGS. 7(A), 7(B) and 7(C) are diagrams illustrating projecting-and-recessed shape example (No. 1) of the first emboss roll 11 and the second emboss roll 12.

FIGS. 8(A) and 8(B) are diagrams illustrating projecting-and-recessed shape example (No. 2) of the first emboss roll 11 and the second emboss roll 12.

DETAILED DESCRIPTION OF THE INVENTION

Embodiments of the present invention will be described below in detail by referring to the attached drawings.

Figure 1:
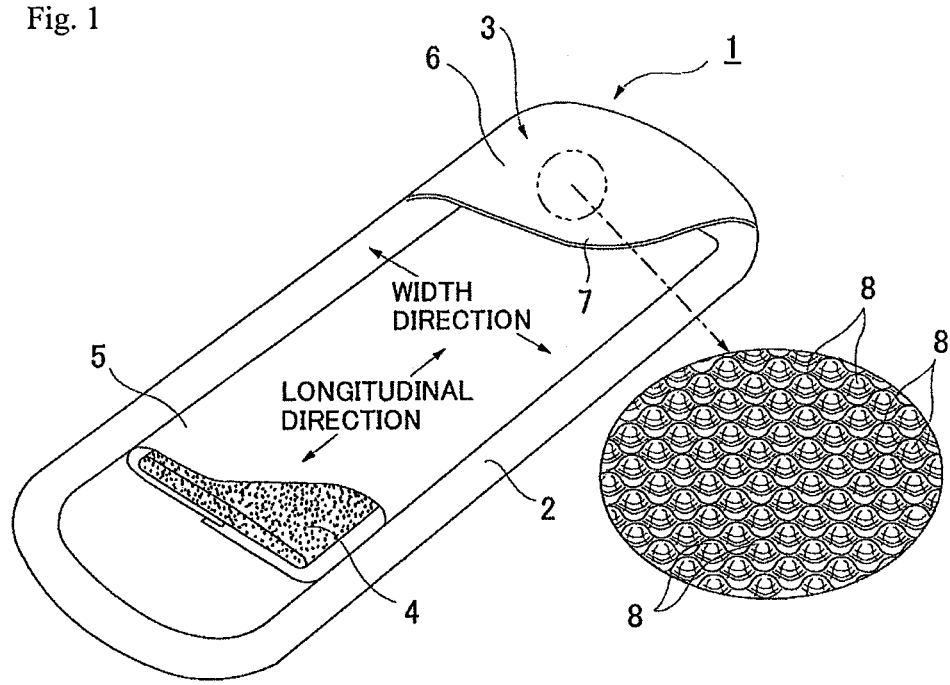
FIG. 1 is a partially broken perspective view of an absorbent article 1 according to the present invention.

A sanitary napkin 1 illustrated in FIG. 1 is offered for applications mainly of a pantiliner, a sanitary napkin, a liner sheet, an incontinence pad and the like and has a structure in which between a non-permeable back-face sheet 2 and a permeable surface sheet 3 (hereinafter simply referred as a surface sheet), an absorber 4 or as illustrated in the figure, the absorber 4 surrounded by a crepe paper material 5 is interposed. In the periphery of the absorber 4, the non-permeable back-face sheet 2 and the surface sheet 3 are joined by adhesive means such as a hot-melt adhesive or the like.

For the non-permeable back-face sheet 2, a sheet material having at least water shielding properties such as polyethylene, polypropylene and the like is used, but other than that, an unwoven-cloth sheet (in this case, the non-permeable back-face sheet is constituted by a water-proof film and an unwoven cloth) can be used after non-permeability is substantially ensured by interposing a water-proof film. Recently, from the viewpoint of prevention of damp feeling, those having moisture permeability tend to be preferably used. For this water-shielding/moisture permeable sheet material, a fine porous sheet obtained by melting and kneading inorganic filler in an olefin resin such as polyethylene, polypropylene and the like so as to mold a sheet and then, by stretching it in a uniaxial or biaxial direction is preferably used.

The surface sheet 3 is formed of an upper layer sheet 6 to which projecting-and-recessed embosses 8 . . . and 9 . . . are given and a planar shaped lower layer sheet 7, in which the bottom face of the recess portion of the upper layer sheet 6 and the lower layer sheet 7 are heat-sealed at a contact surface portion S. This surface sheet 3 will be described in detail later more specifically.

For an absorber 4 interposed between the non-permeable back-face sheet 2 and the surface sheet 3, those obtained by mixing a highly water-absorbing resin in pulp or those mixed with chemical fibers in pulp and also mixed with a highly water-absorbing resin, for example. It is preferable that the absorber 4 is surrounded by a crepe paper material 5 as illustrated in order to maintain the shape, to rapidly diffuse menstrual blood or the like and to prevent return of the menstrual blood or the like once absorbed. For the pulp, those made of chemical pulp obtained from lumber, cellulose fiber such as molten pulp or the like, artificial cellulose fiber such as rayon, acetate or the like can be cited, and softwood pulp with a fiber length longer than hardwood pulp is preferably used in terms of functions and price.

The highly water-absorbing resins include cross-linked polyacrylate substances, self-cross-linked polyacrylate substances, acrylic ester—vinyl acetate copolymer cross-linked saponified substances, isobutylene—maleic anhydride copolymer cross-linked substances, polysulphonic acid cross-linked substances, partially cross-linked water-swellable polymers such as polyethyelene oxide, polyacrylamide and the like. Among them, acrylic acid or acrylate substances excellent in water absorbing capacity and water absorbing speed are preferable. Regarding the highly water-absorbing resin having the water-absorbing performances, water absorbing power and water absorbing speed can be adjusted by adjusting a cross-linking density and cross-linking density gradient in a manufacturing process. The content of the highly water-absorbing resin is preferably 10 to 60%. If the highly water-absorbing resin content is less than 10%, sufficient absorbing capacity cannot be given, while if it exceeds 60%, tangling among pulp fibers is lost, sheet strength is lowered, and breakage, cracks or the like can easily occur.

Figure 2:
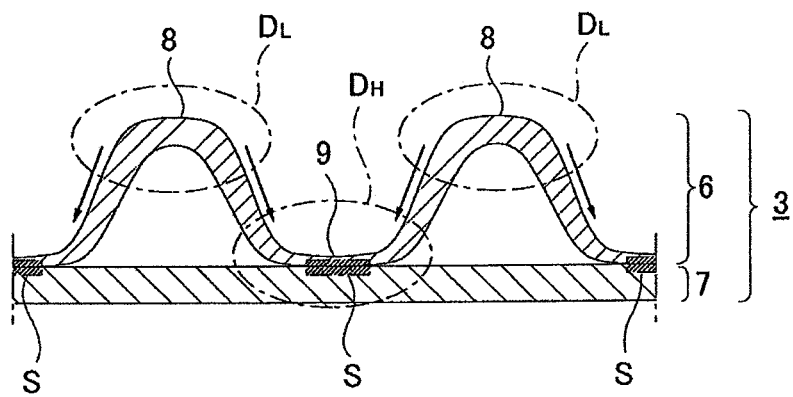
FIG. 2 is an enlarged sectional view of an essential part of a surface sheet 3.

The surface sheet 3 is, as illustrated in FIG. 2, formed of the upper layer sheet 6 to which projecting-and-recessed embosses made of the projecting portions 8, 8 . . . and the recess portions 9, 9 . . . are given and the planar shaped lower layer sheet 7, in which the bottom face of the recess portion of the upper layer sheet 6 and the lower layer sheet 7 are heat-sealed at the contact surface portion S. Combinations of the upper layer sheet 6 and the lower layer sheet 7 include a first example in which both the upper layer sheet 6 and the lower layer sheet 7 are unwoven cloth, a second example in which the upper layer sheet 6 is unwoven cloth and the lower layer sheet 7 is a mesh sheet, and moreover, a third example in which the upper layer sheet 6 is a mesh sheet and the lower layer sheet 7 is unwoven cloth. In the following example, the first example in which the upper layer sheet 6 and the lower layer sheet 7 are both unwoven cloth will be mainly described.

In the aspect of the illustrated projecting-and-recessed embosses, the projecting portions 8, 8 . . . are arranged in the staggered manner and the recess portions 9, 9 . . . are also arranged between the projecting portions 8, 8 . . . in the staggered manner.

The material fibers constituting the upper layer sheet 6 and the lower layer sheet 7 can be synthetic fibers including olefins such as polyethylene, polypropylene or the like, polyesters, polyamides and the like, recycled fibers such as rayon, cupra and the like, and natural fibers such as cotton and the like, and unwoven cloth obtained by appropriate processing methods such as air-through method, spun-race method, spun-bond method, thermal bond method, melt-blown method, needle punch method and the like can be used. Among these processing methods, the spun-race method is excellent in its rich flexibility and drape property, while the air-through method and thermal bond method are excellent in bulkiness and softness. The fiber of the unwoven cloth may be either of long fiber and short fiber, but short fiber is preferable in order to give a texture of towel cloth. Also, in order to facilitate emboss processing, olefin fibers such as polyethylene, polypropylene or the like having a relatively low melting point is preferably used. Also, complex fibers such as a core-sheath type fiber having a fiber with a high melting point as a core and a fiber with a low melting point as a sheath, side-by-side fiber, a divided-type fiber and the like can be preferably used. In these unwoven cloth groups, the most preferably used cloth in the present invention is the air-through unwoven cloth which can be bulky easily. Regarding the composition of the fiber, it is preferable that the upper layer sheet 6 has weight of 5 to 25 g/m$^2$ and fineness of 1.5 to 2.0 dtex and the lower layer sheet 7 has weight of 5 to 30 g/m$^2$ and fineness of 2.0 to 3.0 dtex. It is preferable that the lower layer sheet 7 is set to have relatively higher fiber density. The unwoven cloth should be hydrophilic with a body fluid. Specifically, by using a method of surface treatment of the synthetic fibers such as olefins including polyethylene, polypropylene and the like, polyesters, polyamides and the like with hydrophilizing agent, a method of co-existence and polymerization of a compound having a hydrophilic group such as an oxidation product of polyethylene glycol, for example, in a manufacturing process of the synthetic fiber, a method of treatment using a metal salt such as stannic chloride, partially dissolving the surface to make it porous and precipitating metal hydroxides and the like, the synthetic fiber is swollen or made porous so that a fiber to which hydrophilicity is given by applying a capillary phenomenon is used.

When the upper layer sheet 6 and the lower layer sheet 7 are heat-sealed at the contact surface portion S, since the recess portions 9 of the upper layer sheet 6 are strongly compressed, the projecting portions 8, 8 . . . become low density regions $D_L$, having a relatively low fiber density and the recess portions 9, 9 . . . become high density regions $D_H$ having a relatively high fiber density, and a fiber density gradient from the low density region $D_L$ to the high density region $D_H$ is formed. As a result, if the body fluid is discharged to the surface sheet 3, the body fluid present in the recess portions 8, 8 . . . rapidly moves to the recess portions 9, 9 . . . side by the fiber density gradient, whereby diffusion property of the body fluid becomes favorable, and since the body fluid is not retained on the surface side (the low density region $D_L$ side), a sticky feeling is solved. The collected body fluid is transmitted through the lower layer sheet 7 and is absorbed by the absorber 4.

If the lower layer sheet 7 is a mesh sheet as in the second example cited as a combination example of the upper layer sheet 6 and the lower layer sheet 7, the mesh sheet 7 is preferably subjected to treatment by using a hydrophilizing agent so that the hydrophilicity becomes higher than the upper layer sheet 6. Such giving of the hydrophilicity is accomplished by applying a surfactant (hydrophilizing agent) on the front and back faces of the mesh sheet.

As the surfactant, anionic surfactant, carboxylate, acylated hydrolyzed protein, sulfonate, sulfate ester salt, phosphate ester salt, non-ionic surfactant, polyoxyethylene surfactant, carboxylic ester, carboxylic amide, polyalkyleneoxide block copolymer, cationic surfactant, quaternary ammonium salt, ampholytic surfactant, imidazolinium derivative and the like can be cited, for example, and any other known surfactant to be applied on fibers may be applied.

As a method of applying the above surfactant, application by spraying, coating by gravure printing or flexo printing, curtain coating by using various coaters can be cited, for example. The hydrophilicity can be adjusted by adjusting an application amount of the surfactant. By giving the hydrophilicity gradient, the body fluid present on the upper face of the mesh sheet 7 can be effectively sucked onto the absorber 4 side.

In the case of the first example cited as a combination example of the upper layer sheet 6 and the lower layer sheet 7, the lower layer sheet 7 also functions as a second sheet, but in the case of the second example in which the lower layer sheet 7 is a mesh sheet, a second sheet made of hydrophilic unwoven cloth can be laid on the lower face thereof. For the material of the mesh sheet, olefin resins such as polyethylene, polypropylene and the like, polyamide resins such as polyester, nylon and the like, ethylene—vinyl acetate copolymer (EVA) and the like can be preferably used, for example.

An opening if the mesh sheet is used has an opening area per opening of 0.35 to 0.60 mm$^2$ or preferably 0.47 to 0.54 mm$^2$ and is formed at an opening rate of 10 to 19% or preferably 11 to 14%. If the opening area is less than 0.35 mm$^2$, the opening area is too small and the body fluid remains in the opening wall portion. If the opening area exceeds 0.60 mm$^2$, the body fluid returns through the openings, which is not preferable. On the other hand, if the opening rate is less than 10%, the opening rate is too small and the body fluid discharged onto the surface cannot be rapidly transmitted. Also, if the rate exceeds 19%, return of the body fluid occurs, which is not preferable.

In the sectional structure example illustrated in FIG. 2, a space is generated between the projecting portion 8 of the upper layer sheet 6 and the lower layer sheet 7, but this space may be made such that the space is not substantially present by recovery of the fibers after embossing. If the space is not present and the fibers with the density lower than that on the outer surface side are present, cushion properties are improved, and the body fluid penetrating into the inside smoothly moves to the lower layer sheet 7 side through a capillary phenomenon. Also, in FIG. 2, a stepped portion by reference surfaces 14 and 17 of the emboss rolls 11 and 12, which will be described later, is not generated between the recess portions 9 and the projecting portions 8, but in the illustrated example, since the distance between the recess portion 9 and the projecting portion 8 is small, the stepped portion is lost in actuality by recovery of the fibers. If the recess portions 9 and the projecting portions 8 are separated from each other to a certain degree, a smooth plane is present between the recess portions 9 and the projecting portions 8.

Figure 3:
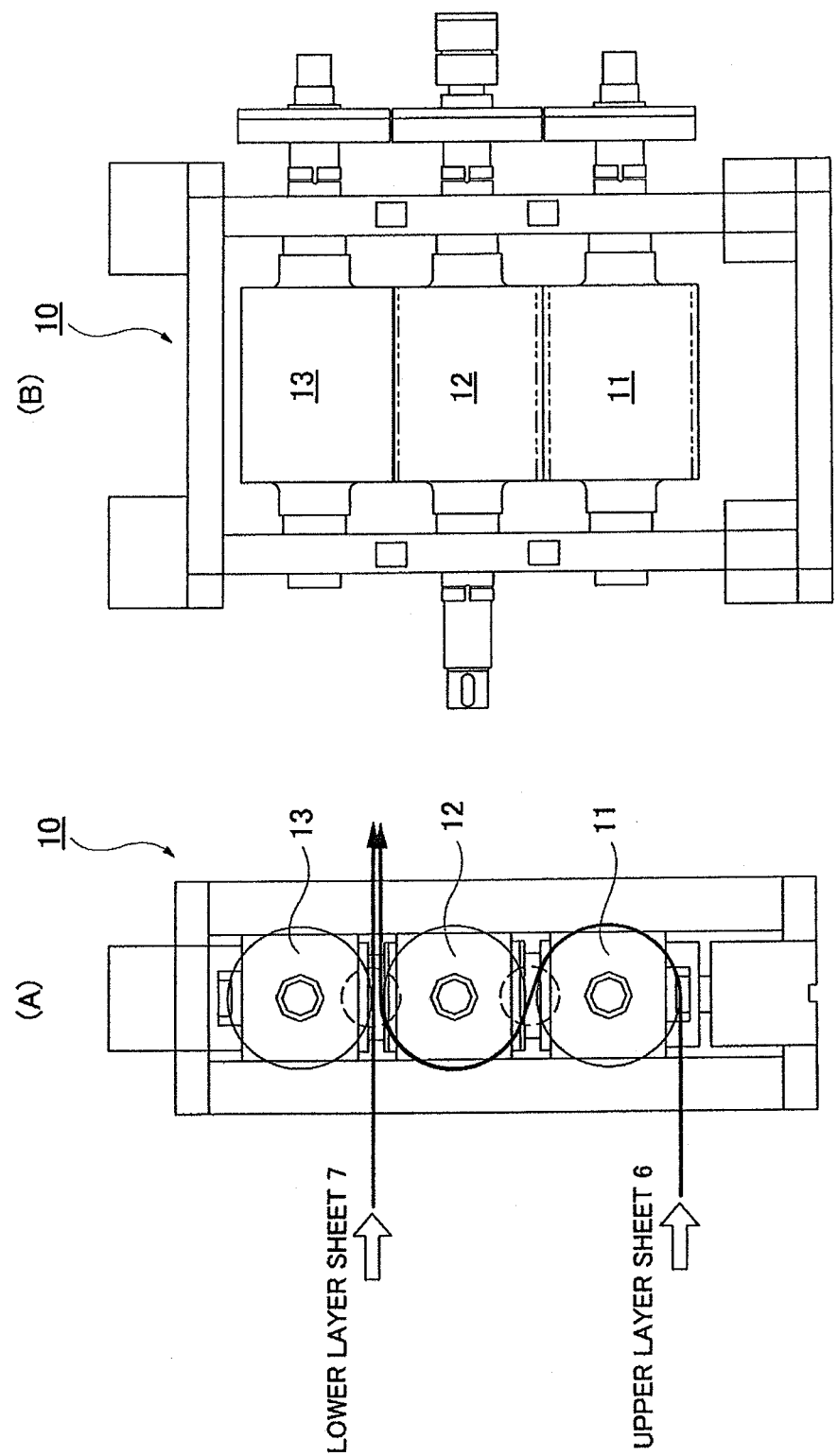
FIG. 3A is a side view and FIG. 3B is a front view illustrating an emboss roller 10.

In manufacture of the above-described surface sheet 3, as illustrated in FIG. 3, an emboss roller apparatus 10 in which the first emboss roll 11, the second emboss roll 12, and an anvil roll 13 having a smooth surface are juxtaposed from the lower stage side in the vertical direction is used. By using the first emboss roll 11 and the second emboss roll 12 as a set and by passing the upper layer sheet 6 between these emboss rolls 11 and 12, the projecting-and-recessed embosses are given, and the upper layer sheet 6 is passed between the second emboss roll 12 and the anvil roll 13 and the lower layer sheet 7 is made to enter between the second emboss roll 12 and the anvil roll 13, and the upper layer sheet 6 and the lower layer sheet 7 are overlapped with each other, while at least one of the second emboss roll 12 and the anvil roll 13 is brought to a state heated to a predetermined temperature, and the bottom face of the recess portion of the upper layer sheet 6 and the lower layer sheet 7 are joined to each other by thermal fusion bonding.

Figure 4:
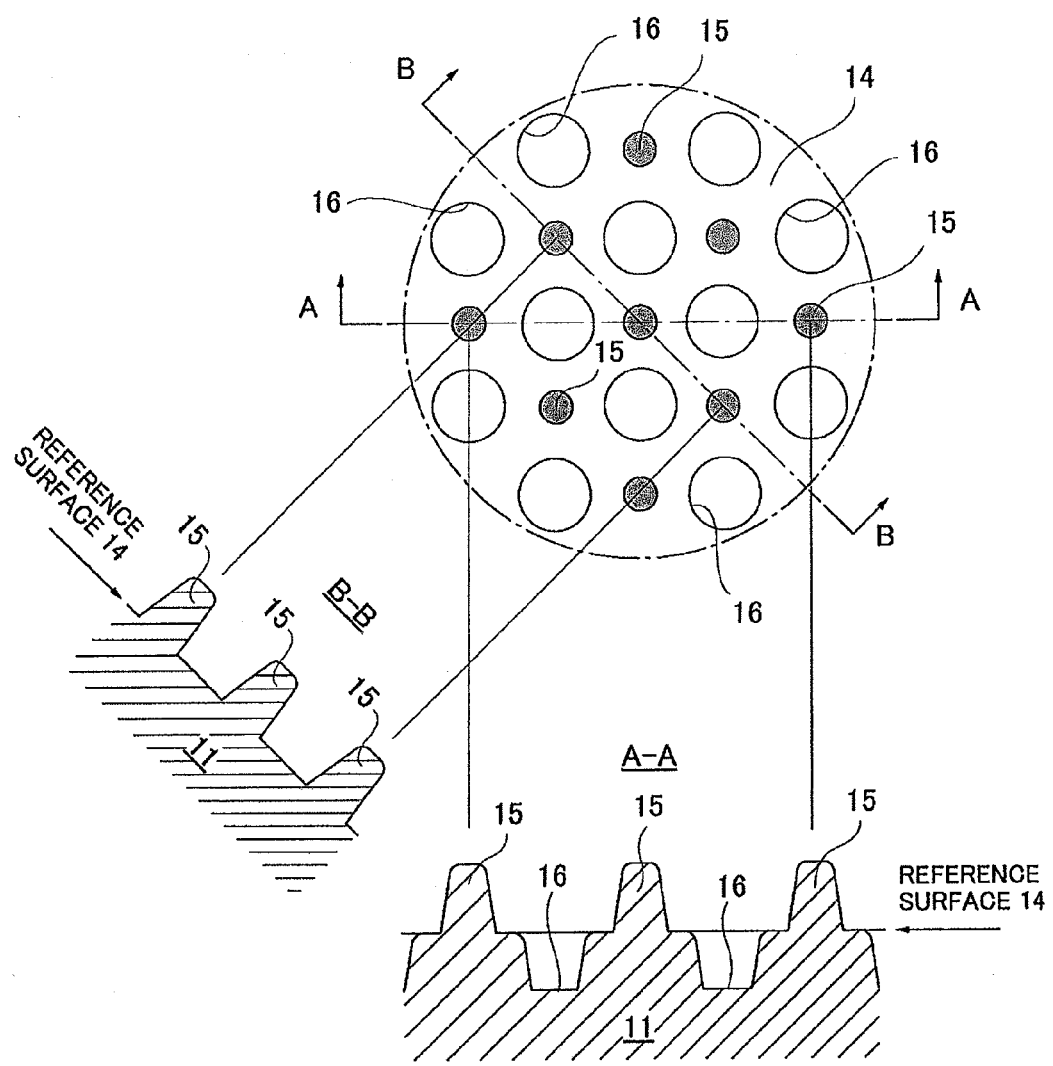
FIG. 4 is a diagram illustrating a projecting-and-recessed shape of a first emboss roll 11.

On the surface of the first emboss roll 11, as illustrated in FIG. 4, projecting portions 15, 15 . . . projecting outward from the reference surface 14 using the reference surface 14 as a boundary and recess portions 16, 16 . . . recessed from the reference surface 14 are provided, and the smooth reference surface 14 is present in the periphery of the projecting portions 15, 15 . . . and the recess portions 16, 16 . . . . Here, the "reference surface" is a surface forming a roll outer surface assuming that the projecting portions 15 and the recess portions 16 are not present.

Figure 5:
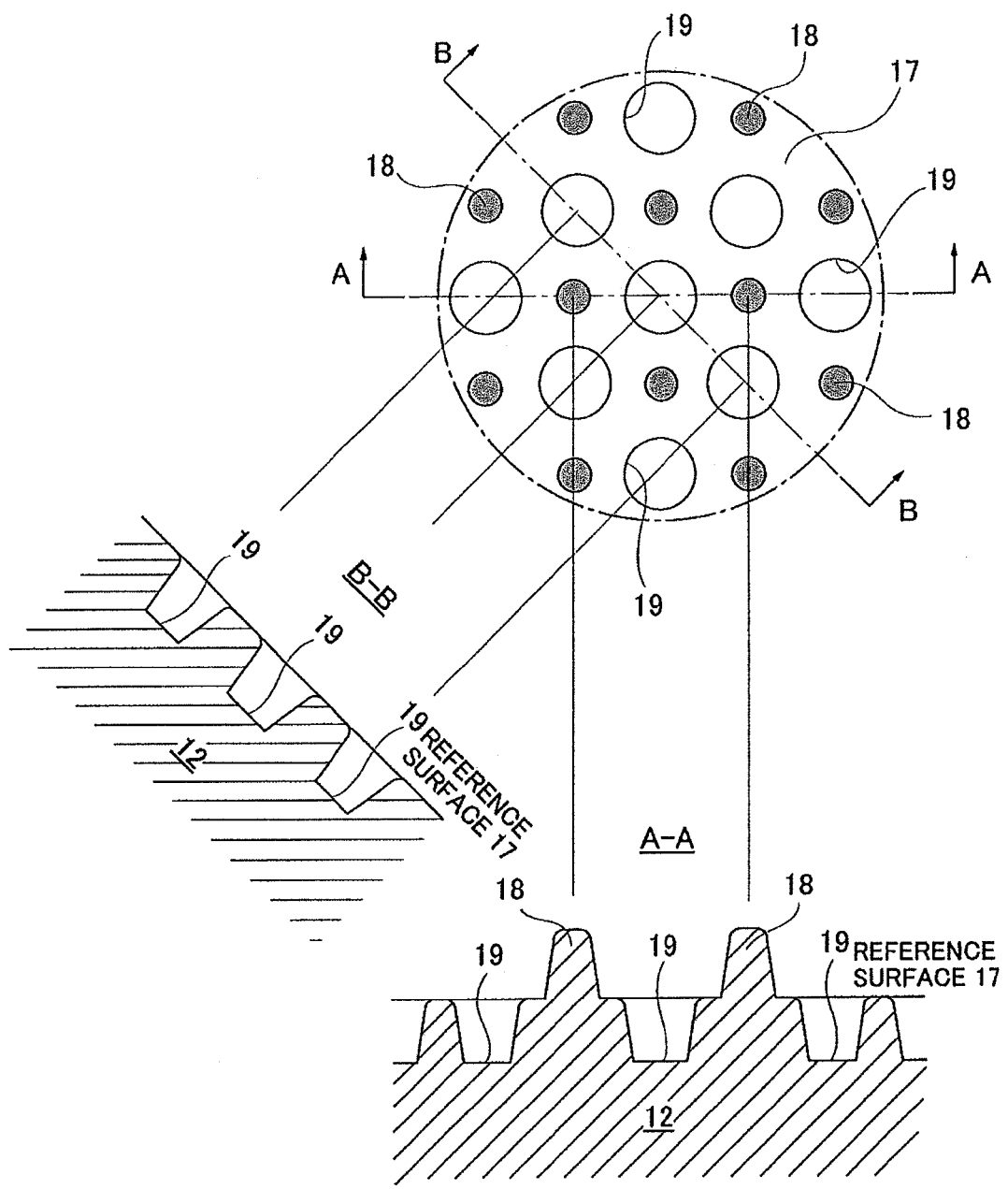
FIG. 5 is a diagram illustrating a projecting-and-recessed shape of a second emboss roll 12.

On the other hand, on the surface of the second emboss roll 12, too, as illustrated in FIG. 5, projecting portions 18 projecting outward from a reference surface 17 by using the reference surface 17 as a boundary and meshed with the recess portions 16 of the first emboss roll 11 and recess portions 19 recessed from the reference surface 17 and meshed with the projecting portions 15 of the first emboss roll 11 are provided, and the smooth reference surface 17 is present in the periphery of the projecting portions 18 and the recess portions 19.

Figure 6:
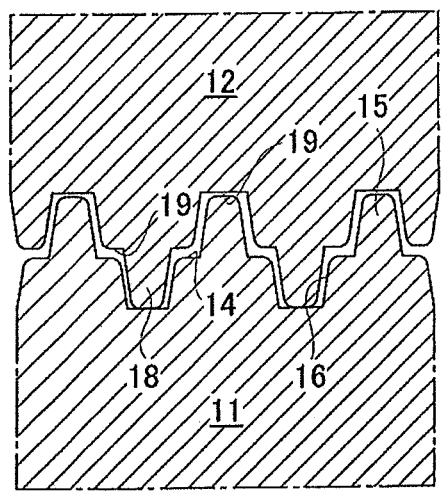
FIG. 6 is an enlarged sectional view of an essential part illustrating a meshed state between the first emboss roll 11 and the second emboss roll 12.
Figure 9:
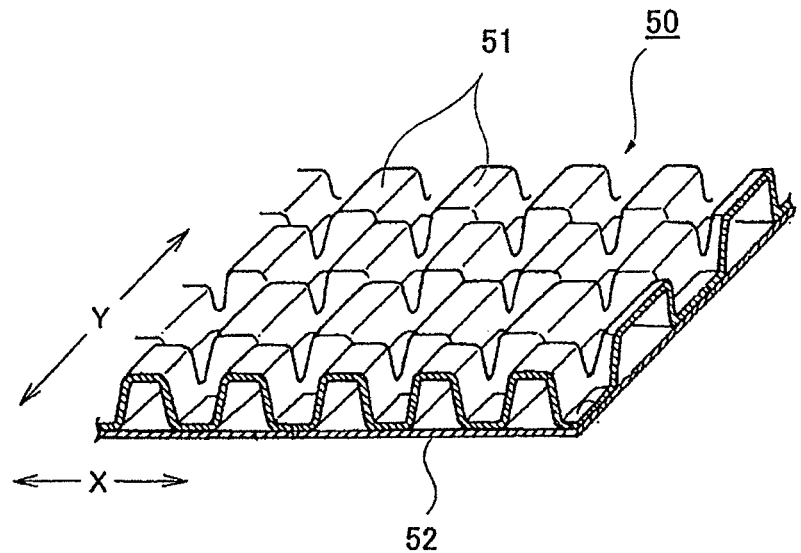
FIG. 9 is a perspective view illustrating a surface sheet 50 according to Japanese Unexamined Patent Application Publication No. 2004-174234.
Figure 10:
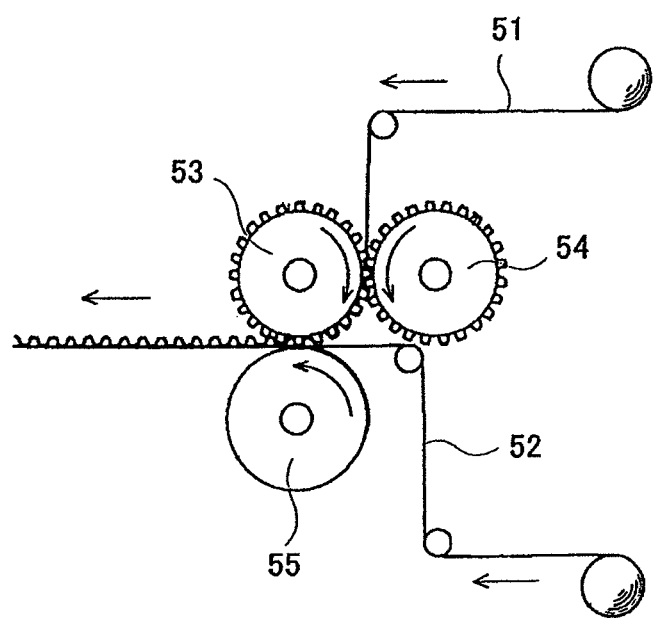
FIG. 10 is an outline diagram illustrating a producing method thereof.
Figure 11:
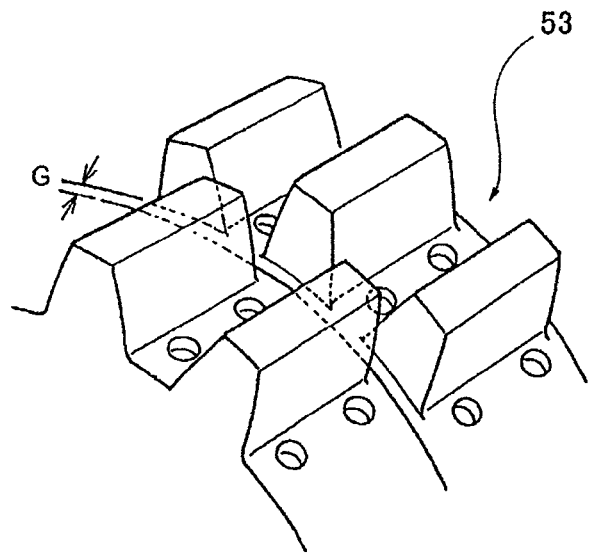
FIG. 11 is an enlarged perspective view of an essential part illustrating the first roll 53.
Figure 12:
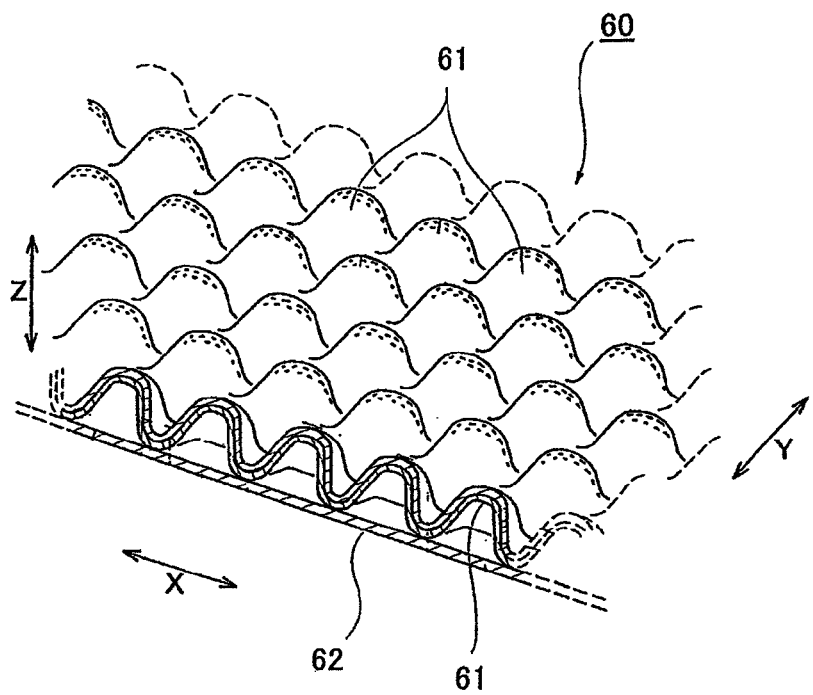
FIG. 12 is a perspective view illustrating a surface sheet 60 according to Japanese Unexamined Patent Application Publication No. 2009-50538.
Figure 13:
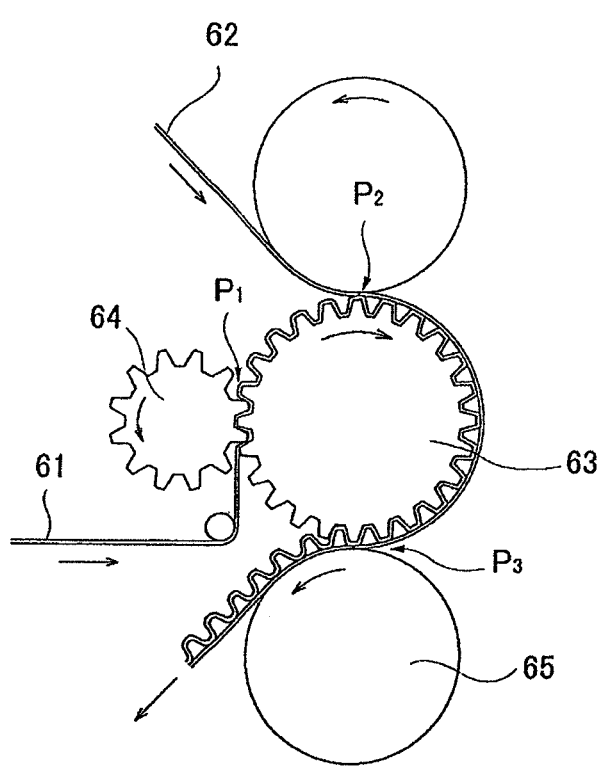
FIG. 13 is an outline diagram illustrating a producing method thereof.

The first emboss roll 11 and the second emboss roll 12 are, as illustrated in FIG. 6, formed such that the projecting portions 15 of the first emboss roll 11 are meshed with the recess portions 19 of the second emboss roll 12 and the recess portions 16 of the first emboss roll 11 are meshed with the projecting portions 18 of the second emboss roll 12, and in the periphery of the meshed parts between the projecting portions 15 and 18 and the recess portions 16 and 19, a horizontal planar shaped stepped portion is formed by the reference surfaces 14 and 17.

The anvil roll 13 is a smooth roll with a smooth surface not having projections or recesses on the outer peripheral face and formed such that the distal end faces of the projecting portions 18, 18 . . . of the second emboss roll 12 are in contact with or brought into contact with it through an extremely slight gap. At least one or preferably both of the second emboss roll 12 and the anvil roll 13 are brought into a state heated to a predetermined temperature, and by crimping the surface sheet 3 while heating the same by the projecting portions 18, 18 . . . of the second emboss roll 12 and the anvil roll 13, the bottom face of the recess portion of the upper layer sheet 6 and the lower layer sheet 7 are joined to each other by thermal fusion bonding.

Specifically, in FIG. 3A, the upper layer sheet 6 is introduced to the lower face side of the first emboss roll 11 on the lowermost stage from the left side in the figure and in a state in which the sheet circles only a half cycle, the projecting-and-recessed embosses are given when passing between the first emboss roll and the second emboss roll 12, and then, after circling only a half cycle of the second emboss roll 12, the sheet enters between the second emboss roll and the anvil roll 13 and is conveyed in the right direction in the figure.

On the other hand, the lower layer sheet 7 is introduced between the second emboss roll 12 and the anvil roll 13 from the left side in the figure, the upper layer sheet 6 and the lower layer sheet 7 are overlapped with each other between the second emboss roll 12 and the anvil roll 13, and the bottom face of the recess portion of the upper layer sheet 6 and the lower layer sheet 7 are joined to each other by thermal fusion bonding.

In this emboss roller 10, after the projecting-and-recessed embosses are given by the first emboss roll 11 and the second emboss roll 12, during a process of conveyance along the periphery of the second emboss roll 12, the upper layer sheet 6 is pushed into the recess portion 19 of the second emboss roll 12, and thus, it is not necessary to bring the sheet into close contact with the peripheral face of the roll by a suction force for retention as in the invention described in Patent Document 2.

In the above embodiment, the projecting-and-recessed emboss pattern has the projecting portions 8, 8 . . . arranged in the staggered manner with respect to the upper layer sheet 6 and the recess portions 9, 9 . . . arranged also in the staggered manner between the projecting portions 8, 8 . . . , but in the case of the emboss roller 10 according to the present invention, since the projecting portions 15, 15 . . . and the recess portions 16, 16 . . . are formed in an arbitrary pattern on the first emboss roll 11 and the recess portions 19 corresponding to the projecting portions 15, 15 . . . and the projecting portions 18, 18 . . . corresponding to the recess portions 16, 16 . . . are formed on the second emboss roll 12, it is possible to give an arbitrary projecting-and-recessed emboss pattern. For example, an example illustrated in FIG. 7A is an example of the projecting-and-recessed emboss pattern in the linear waveform in one direction, an example illustrated in FIG. 7B is an example of the projecting-and-recessed emboss pattern in the wavy waveform in one direction, FIG. 7C is a projecting-and-recessed emboss pattern in which elongated oval coin shaped embosses are aligned and arranged, FIG. 8A is a projecting-and-recess emboss pattern in which elongated oval coin shaped embosses are arranged in the lattice shape, and FIG. 8B is a projecting-and-recessed emboss pattern in which three circular embosses are aligned and arranged as one set. Various projecting-and-recessed emboss patterns are possible other than the above.

In the above embodiment, the example was cited in which the surface sheet 3 is formed of the upper layer sheet 6 to which the projecting-and-recessed embosses made of the projecting portions 8, 8 . . . and the recess portions 9, 9 . . . are given and the planer shaped lower layer sheet 7, and the bottom face of the recess portion of the upper layer sheet 6 and the lower layer sheet 7 are heat-sealed at the contact surface portion S, but only the upper layer sheet 6 can be used as the surface sheet 3. In this case, the emboss roller 10 is made of the first emboss roll 11 and the second emboss roll 12, and the emboss roller in which the anvil roll 13 is omitted is used.

The invention claimed is:

1. A method for producing a surface sheet made of an upper layer sheet comprising nonwoven fabric to which projecting-and-recessed embosses are imparted and a planar shaped lower layer sheet comprising nonwoven fabric or a mesh sheet and in which a bottom face of a recess portion of the upper layer sheet is heat-sealed with the lower layer sheet, the method performed with an emboss roller having a first emboss roll and a second emboss roll formed as a set for imparting projecting-and-recessed embosses to the surface sheet by passing the surface sheet between the emboss rolls, wherein on a surface of the first emboss roll, a projecting portion projects outward from a reference surface with the reference surface as a boundary and a recess portion is recessed from the reference surface, and a smooth reference surface is present in the periphery of the projecting portion and the recess portion, wherein on a surface of the second emboss roll, a projecting portion projects outward from the reference surface with the reference surface as a boundary and meshes with the recess portion of the first emboss roll and a recess portion is recessed from the reference surface and meshes with the projecting portion of the first emboss roll, and a smooth reference surface is present in the periphery of the projecting portion and the recess portion, and wherein the meshing portions of the projecting portion and the recessed portion of the first emboss roll and the second emboss roll are such that, between adjacent meshing portions, a horizontal planar shaped stepped portion is present due to the reference surfaces, the method comprising:

preparing the surface sheet by pressing the upper layer sheet between the first emboss roll and second emboss roll wherein an anvil roll having a smooth surface is arranged adjacent to the second emboss roll, and at least one of the second emboss roll and the anvil roll is brought into a state heated to a predetermined temperature, whereby the projecting-and-recessed embosses are imparted to the upper layer sheet;

conveying the upper layer sheet having the projecting-and-recessed embosses, between the second emboss roll and the anvil roll while introducing the lower layer sheet between the second emboss roll and the anvil roll with the upper layer sheet overlapping the lower layer sheet whereby a bottom face of the recess portion of the upper layer sheet and the lower layer sheet are heat-sealed together; and setting, in the emboss roller, a close distance between the meshing portions of the projecting portions and the recessed portions of the first emboss roll and the second emboss roll, wherein said stepped portion, which results from the reference surfaces of the first emboss roll and the second emboss roll that are present between the recessed portions and the projecting portions, is eliminated by a recovery of fibers.

* * * * *